United States Patent [19]

McGovern et al.

[11] Patent Number: 4,675,342
[45] Date of Patent: Jun. 23, 1987

[54] COCKROACH REPELLENTS

[75] Inventors: Terrence P. McGovern, Bowie, Md.; Carl E. Schreck; George S. Burden, both of Gainesville, Fla.

[73] Assignee: The United States of America as represented by the Secretary of Agriculture, Washington, D.C.

[21] Appl. No.: 856,871

[22] Filed: Apr. 23, 1986

Related U.S. Application Data

[60] Division of Ser. No. 625,328, Jun. 27, 1984, abandoned, which is a continuation-in-part of Ser. No. 488,530, May 3, 1983, abandoned, which is a continuation of Ser. No. 349,948, Feb. 28, 1982, abandoned, which is a continuation of Ser. No. 240,446, Mar. 4, 1981, abandoned, which is a division of Ser. No. 8,814, Feb. 2, 1979, Pat. No. 4,291,041.

[51] Int. Cl.$^4$ .......................................... A01N 37/18
[52] U.S. Cl. .................................... 514/613; 514/919; 514/617; 514/622; 424/DIG. 10
[58] Field of Search ................ 514/613, 919, 617, 622

[56] References Cited

U.S. PATENT DOCUMENTS

| | | | |
|---|---|---|---|
| 2,350,324 | 6/1944 | Coleman et al. | 514/613 |
| 2,677,705 | 5/1954 | Utzinger | 564/123 |
| 3,246,975 | 4/1966 | Hopkins et al. | 546/226 X |
| 3,277,171 | 10/1966 | Hopkins | 546/226 X |
| 3,296,306 | 1/1967 | Doering et al. | 546/226 X |
| 3,480,663 | 11/1969 | Thiele | 546/205 X |
| 4,054,604 | 10/1977 | Bernady et al. | 564/123 |
| 4,216,172 | 8/1980 | Heine et al. | 564/123 X |
| 4,248,859 | 2/1981 | Rowsell et al. | 564/123 X |
| 4,283,420 | 8/1981 | Pigerol et. | 564/123 |
| 4,291,041 | 9/1981 | McGovern et al. | 514/613 |
| 4,366,317 | 12/1982 | Haut et al. | 564/123 X |
| 4,530,935 | 7/1985 | McGovern et al. | 514/613 |

FOREIGN PATENT DOCUMENTS

| | | | |
|---|---|---|---|
| 1106757 | 5/1961 | Fed. Rep. of Germany | 564/123 |
| 3019293 | 12/1981 | Fed. Rep. of Germany | 564/123 |
| 1351761 | 1/1972 | United Kingdom | 564/123 |
| 1411786 | 10/1975 | United Kingdom | 564/123 |

OTHER PUBLICATIONS

Briel, Chem. Abst. 82:93905e (1974).
Johnson et al., Chem. Abst. 70:28589t.
McGovern et al., Mosquito News, vol. 38, No. 4, pp. 510–514 (Dec. 1978) in SN 488,530.
McGovern et al., Mosquito News, vol. 38, No. 3, pp. 346–349 (Sep. 1978) in SN 488,530.
Needles et al., J. Org Chem 31(3), 989–90 (1966).
Yu et al, CA 59:7490f.
Speziale, CA 61:590f.
Bar Zeev et al, CA 75:75291c.
Johnson et al, CA 70:28589t.
Carson et al, CA 75:5468s.
Briel, CA 82:93905e.
Borowitz et al, CA 88:22321z.
Schreck, C., et al, J. Med. Entomol., 14(5), 589–591 (1978).
Smith, N., et al., Mosquito News, 36(1), 36–38 (1976).
Alexander, B., et al., J. Econ. Entomol., 56(1), 58–60 (1963).
McGovern, T., et al., Mosquito News, 35(2); 204–210 (1975).
McGovern, T., et al., J. Econ. Entomol., 67(5), 639–640 (1974).
Gouck, H., et al, J. Econ. Entomol., 50, 175–177 (1957).

Primary Examiner—Jerome D. Goldberg
Assistant Examiner—F. L. Krosnick
Attorney, Agent, or Firm—M. Howard Silverstein; David G. McConnell; William E. Scott

[57] ABSTRACT

A number of novel carboxamides were found to be effective insect repellents and some were found to be highly effective as cockroach repellents.

6 Claims, No Drawings

COCKROACH REPELLENTS

This application is a divisional of application Ser. No. 625,328, filed June 27, 1984, now abandoned which is a continuation-in-part of application Ser. No. 488,530, filed May 3, 1983, now abandoned, which is a file wrapper continuation of application Ser. No. 349,948, filed Feb. 28, 1982, now abandoned, which is a continuation of application Ser. No. 240,446, filed Mar. 4, 1981, now abandoned, which is a division of application Ser. No. 8,814, filed Feb. 2, 1979, now U.S. Pat. No. 4,291,041.

BACKGROUND OF THE INVENTION

1. Field of the Invention

This invention relates to insect repellents and more particularly to certain novel carboxamides containing an alicyclic moiety and their use as insect repellents.

2. Description of the Art

There is a continuing need for insect repellents or formulations thereof that are significantly more effective or longer lasting than those now in use. All of the repellents now in use for application to the skin have disadvantages, that is, they are not effective for long enough periods of time and are subject to loss by abrasion, evaporation, absorption, and immersion in water. Moreover, all cause a stinging sensation when they contact the eyelids and lips, and are effective only when they are present on the skin or clothing in relatively large quantities. Mosquitoes, sand flies, black flies, stable flies, tsetse flies, gnats, and tabanids are among the many species of biting fly that cause annoyance and distress throughout the world. Many species of biting insects spread human and animal diseases. There are many areas throughout the world in both developed and developing nations where the use of protective clothing and repellents is the only means available to individuals for personal protection. Deet (N,N-diethyl-m-toluamide) has proved to be the most outstanding all-purpose individual repellent yet developed (Proceedings of a Symposium, University of Alberta, Edmonton, Canada, May 16-18, 1972, Defense Research Board, Ottawa, Canada, 1973. DR-217: 109-113). Deet was reported as a promising repellent in 1954 (Journal of Organic Chemistry, 19, 493, 1954). Since that time, no repellent has been reported as being superior to deet as an all-purpose repellent despite a continuing search for such a chemical.

There is also a definite need for cockroach repellents or formulations thereof that are effective and long lasting. Application of an efficient repellent to potential harborage areas of shipping cartons and assorted containers can prevent the distribution or movement of cockroaches from one area to another. A repellent can be used either alone or as one phase of an integrated control program in buildings, food- and drink-vending machines, assorted equipment, transportation systems, and other areas where cockroaches may be a problem. An effective cockroach repellent would act as an alternate non-insecticidal means of reducing insect depredation from that of conventional insecticides and would be particularly useful in areas where the application of toxicants would be severely limited. Its importance as a control agent continues to increase as the cockroach continues to develop insecticide resistance. Although the potential for such repellent chemicals in cockroach control has been recognized for sometime, few effective repellents have been reported and even fewer practical demonstrations of the use of such chemicals have been described (Soap and Sanitary Chemistry, 21, 129 and 157, 1945; Industrial Engineering Chemistry, 43, 1588, 1951; Journal of Economic Entomology, 45, 133, 1952; Pest Control, 28 (6), 14, 1960; Journal of Economic Entomology, 53, 805, 1960; Pest Control, 28 (8), 44, 46, 48, 50, 1960; Pest Control, 29 (6), 32, 1961; Pest Control, 30 (7), 14, 16, 18, 1962; Journal of Economic Entomology, 63, 429, 1970; Journal of Economic Entomology, 64, 576, 1971; Journal of Economic Entomology, 67, 639, 1974; Journal of Economic Entomology, 67, 71, 1974; Journal of Medical Entomology, 12, 259, 1975; Journal of Economic Entomology, 12, 387, 1975; Production Research Report Number 164, USDA, ARS, 1976).

SUMMARY OF THE INVENTION

An object of this invention is to provide a class of compounds that is useful as insect repellents.

Another object of this invention is to provide a class of compounds that is useful as cockroach repellents and that can be readily synthesized from commercially available intermediates.

Still another objective is to provide cockroach repellents that are more effective than those reported previously.

A further object is to provide a means to control insects and more effectively with less hazard to man.

A still further object is to provide a cockroach repellent that can be used in conjunction with other control agents in an integrated program.

According to this invention, the above objects are accomplished by a number of novel carboxamides of the following formula having from 5 to 18 carbon atoms, suitable compositions which incorporate the carboxamides, and methods of using them as insect repellents:

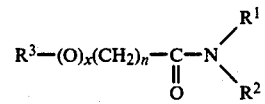

wherein $R^3$ is a saturated or an unsaturated alicyclic ring moiety, either unsubstituted or substituted with lower alkyl or halogen; a substituted or unsubstituted bicyclic ring moiety; straight- or branched-chain alkyl having from 1 to 9 carbon atoms, or straight- or branched-chain alkenyl having from 2 to 8 carbon atoms, x is zero or the positive integer one; n is zero or the positive integer one, two, or three, and each of $R^1$ and $R^2$ is lower alkyl.

Ordinarily, $R_3$ is one of the following alicyclic moieties

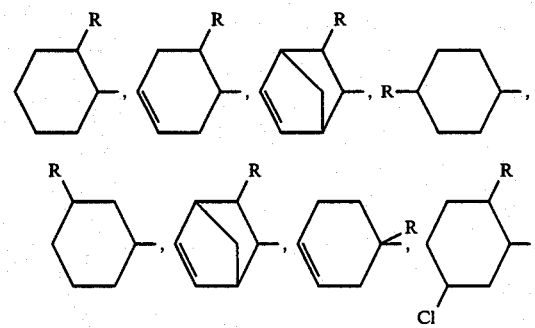

-continued

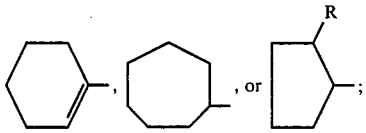

wherein R is hydrogen or lower alkyl, or R³ is

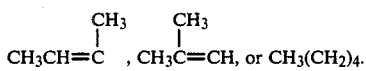

For the purposes of this invention the term lower alkyl means alkyl groups containing from 1 to 5 carbon atoms, either straight- or branched-chained.

Preferred for their outstanding repellency are those compounds of the formula wherein R₃ is

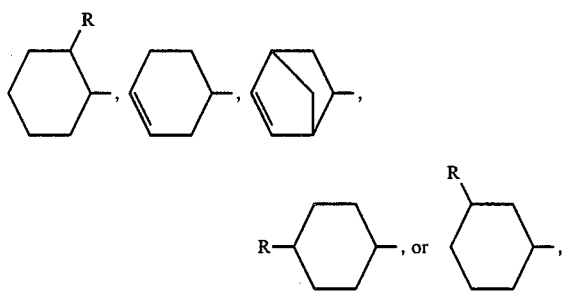

wherein R is hydrogen or lower alkyl or R³ is

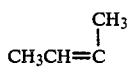

and R¹ and R² are individually methyl, ethyl, propyl, or butyl.

DESCRIPTION OF THE INVENTION

Many of these compounds are more effective than presently available repellents, many are effective against a wide variety of insects, and many of these compounds completely repel the German cockroach *Blattella germanica* (L.) for prolonged periods under stringent test conditions. This species is among the most difficult of cockroach species to control.

The compounds of this invention are useful as insect repellents and are particularly effective against many Dipteran and many Blattaria.

The novel compounds of this invention are especially effective in repelling a wide variety of insects such as ticks, chiggers, cockroaches, and biting diptera such as mosquitoes, stable flies, deer flies, black flies, and sand flies. Certain novel amides reported in this invention are about equally as effective as deet against mosquitoes and are significantly more repellent than deet against other biting flies when tested on skin. The skin test is the obvious critical test when one considers personal protection; however, clothing repellents are also very important especially in areas of heavy mosquito infestations (The Journal of the American Medical Association, 196, 253, 1966). Certain amides of this invention provide exceptional protection against mosquitoes when applied to cloth.

The amides were synthesized as follows: the appropriate acid chloride was slowly added with stirring to an anhydrous ether solution of the amine cooled in an ice bath (either the amine itself or pyridine was used as a hydrochloric acid scavenger). The reaction mixture was allowed to warm to room temperature and then allowed to stand for several hours, usually overnight. The amides were isolated by routine extraction procedures and purified by distillation under high vacuum. Purity was checked by gas chromatographic analysis.

A typical procedure is illustrated by the following description of the synthesis of N,N-diethyl-3-cyclohexylpropanamide: 3-cyclohexylpropanoyl chloride, 174.0 grams (1.0 mole) was added dropwise to an ice cold solution (0° to 10° C.) of N,N-diethylamine, 161.0 grams (2.2 mole) in one liter of anhydrous ether. The solution was stirred during the addition and then allowed to warm to ambient temperature and to stand overnight. The crude product was washed sequentially with water, 5% hydrochloric acid, 10% sodium carbonate and with a saturated salt solution until the wash was neutral to litmus paper. After drying over anhydrous magnesium sulfate and filtering, the solvent was removed under reduced pressure. The crude amide was distilled under high vacuum to give 198.1 grams of product (b.p. 103° C./0.5 mm Hg; $n_D^{25}$ 1.4740).

The physical constants of some of the compounds are presented in Table 1.

The repellent activity of the amides of the present invention was demonstrated by practical laboratory and field tests against mosquitoes and a variety of other biting diptera. The effectiveness of the repellents was determined by directly comparing their repellency with that of deet in tests on skin and with dimethyl phthalate in tests on cloth.

In the following description of the testing procedures the first confirmed bite is defined as a bite followed by another within thirty minutes.

For the purposes of this invention, the compounds were tested against mosquitoes and other biting diptera as solutes in alcohol, acetone, or other volatile solvent. However, other compatible liquid or solid carriers may also be used.

TESTING PROCEDURES

Stable Flies

The repellents were applied as 1-ml aliquots of a 25% ethanol solution and spread evenly over the forearm of a subject from wrist to elbow. Since the ethanol solution was formulated on a weight-volume basis, 250 mg of repellent was applied to the forearm in each test. The most promising compounds (those equal to or better than the deet standard at the 25% dosage) were then tested as 12.5% and 6.25% ethanol solutions.

The evaluations were carried out in an outdoor cage (103 cm square and 133 cm high) constructed of aluminum and having a solid top and bottom and screen wire on four sides. Four of the sides had port openings covered with 30.5-cm (12-in.) tubular cloth stockinettes. The centers of the ports were 30 cm from the bottom of the cage, which rested on a table 80 cm high. One arm each of up to four treated subjects at a time could be inserted through the ports into the cage.

Approximately 12,000 *S. calcitrans* pupae were placed in cups and allowed to emerge in the test cage over an 8-day period. The tests were started the 4th day, when approximately 8000 flies had emerged. The remaining 4000 that emerged over the next four days maintained a relatively stable population in respect to numbers and avidity. Citrated beef blood on a cotton pad was offered for 45 minutes each day after the repellent tests were completed. This short-term feeding period provided a small but adequate food intake, and avidity was not reduced as a result of complete engorgement. Results obtained when an untreated forearm was inserted into the test cage before and during the tests each day gave a measure of the avidity of the flies, though it was impossible to count the attacks on the untreated arm.

The effectiveness of each chemical was determined by the protection time; that is, the time between treatment and the first confirmed bite. Therefore, 30 minutes after the application of the test chemical and every 30 minutes thereafter, the treated arms were inserted into the test cage for three minutes unless bites occurred sooner.

Since test subjects differ in attractiveness and insects differ in avidity, the best measure of the effectiveness of a repellent is its ratio of protection time vs. that of a standard repellent used in similar conditions. Deet was the standard in all of the tests reported here. It was paired with each of the other candidate repellents in ten different test series.

The experimental design used was a round-robin series in which each repellent was paired concurrently against another repellent on the arms of a subject. An adjusted average protection time that allowed for individual variation between test subjects and test conditions was then computed (Soap and Chemical Specialties, 33, 115-117 and 129-133, 1957).

Black Flies

The principal test site was in the vicinity of Kidney Pond, Baxter State Park, Maine. Meadows bordered by fast moving mountain streams and an abundance of wildlife provided optimum breeding conditions in this area. Several species of blackflies were represented in the population attacking four test subjects. Of these, the two most abundant were identified as *Simulium venustum* Say and *Prosimulium mixtum* Syme and Davis. Repellents were applied as 1-ml aliquots of a 12.5 or 25% ethanol solution and spread evenly over the forearm of a subject from wrist to elbow. The ethanol solution was formulated on a weight-volume basis, so either 125 or 250 mg of repellent was applied in each test.

Treated arms were continuously exposed to the natural populations of flies. Subjects intermittently moved about with arms raised or on hips, squatted, or sat down for brief periods of five to ten minutes. These positions, coupled with slow walking and standing every few minutes, appeared to be attractive to black flies (Simulids and Prosimulids) and were used as standard procedure in all tests. Head-nets and gloves were worn by the test subjects to prevent attack on exposed untreated parts of the body.

Two series of round-robin tests were conducted in the spring of 1977 using 12.5 or 25% solutions of repellent in ethanol; one series was conducted during June 1978 using a 25% solution of repellent in ethanol. The effectiveness of each chemical was determined by the protection time, i.e., the time between treatment and the first confirmed bite. Since test subjects differ in attractiveness and insects differ in avidity, the best measure of the effectiveness of a repellent is the ratio of its protection time to that of a standard repellent under similar conditions. Deet was the standard repellent in these tests.

In the round-robin test each repellent was paired with each other repellent on the arms of a subject (four and five replicates). An adjusted average protection time that allowed for individual variations between test subjects and test conditions was then computed. Black fly landing rates ranged from 14 to 40 per minute during the test period.

Deer Flies

The compounds and the standard repellent, deet, were tested on the forearms of human subjects against natural populations of deer fly, *Chrysops atlanticus*. The materials were formulated as 25% ethanol solutions and applied at the rate of 1 ml per forearm. The field tests were conducted along logging roads adjacent to the marshes of the Ogeechee River at Richmond Hill, Ga., where *C. atlanticus* populations occur in great numbers annually. Since the flies are attracted to motion, the test subjects continually walked while exposing their treated arms to the flies. The tests were terminated when a confirmed bite was received. The chemicals were evaluated in round-robin tests with five compounds and a deet standard in each series. During the three week test period the landing rate averaged 33 flies/man and ranged from 13 to 54/man.

Sand Flies

Two test sites were used, one at Yankee Town, Fla. on the Gulf coast and one at Parris Island, S.C. The repellents were applied as 25% solutions in ethanol on the forearms (wrist to elbow) of test subjects. Because of the limited period of insect activity (early morning or late afternoon to dusk) the subjects were pretreated two hours prior to the test period to effect aging of the repellents. The repellents were evaluated against the standard repellent, deet, in paired tests (three applications). A test repellent was applied to one arm of a subject and deet to the other. Effectiveness was determined by the number of bites received during the test period. A control (no repellent treatment) was included in each test to ascertain the level of insect pressure.

Mosquitoes

Tests on skin

For laboratory tests, 1 ml of a 25% ethanol solution of the repellent was spread evenly over the forearm of the subject. The treated forearms were exposed to about 1500 female laboratory reared *Aedes aegypti* or *Anopheles quadrimaculatus* mosquitoes in cages. Effectiveness was based on complete protection, that is, the time between treatment and the first confirmed bite. The effectiveness of the compounds was compared to that of the standard repellent, deet. The chemicals were tested in a round-robin series in a balanced incomplete block design in which each repellent in the series was paired against each other repellent in the series on opposite arms of a given number of subjects.

The field tests were conducted at sites adjacent to Mosquito Lagoon near New Smyrna Beach, Fla. The repellents were applied in the same manner as for the laboratory tests. The treated arms were exposed continuously to the natural population of mosquitoes until the first confirmed bite was received. Protective clothing and head nets were worn by the test subjects to protect against attack on exposed untreated parts of the body. The experimental design used was a balanced incomplete block as in the laboratory tests.

Tests on cloth

Test materials were applied at the rate of 3.3 g of compound per 0.1 $m^2$ cloth to a measured portion (0.03 $m^2$) of a cotton stocking as 10% solutions in acetone or other volatile solvent. After two hours, the treated stocking was placed over an untreated nylon stocking on the arm of a human subject and exposed for one minute in a cage containing about 1500 five- to eight-day old *A. aegypti* or *A. quadrimaculatus*. The test exposure was repeated at 24 hours and then at weekly intervals until five bites were received in one minute. Days to the first bite and to five bites were recorded. Between tests, the treated stockings were placed on a rack at room temperature, and evaporation was allowed to continue. A standard repellent, dimethyl phthalate, was tested concurrently and was effective for 11 to 21 days against both mosquito species.

The merits of the present invention are illustrated in the results shown in the tables.

The data in Table 2 show compounds 2, 7, 20, 33, 34, 47, and 49 were more active against the stable fly than the deet standard at all concentrations tested. Compounds 20 and 34 were significantly more effective than deet at all three dosages (0.05% level of confidence). Compounds 21 and 35 were more active than deet at two concentrations and equal to it at the lowest concentration tested. The repellent effect of certain of these chemicals was as much as 4.5 x that of deet and provided protection up to nine hours; the protection time of deet ranged from two to three hours. Data for compounds 4, 6, 17, 18, 19, 31, and 45 are shown to illustrate the unpredictability of repellent activity of closely related chemicals.

The data in Table 3 show all eight compounds and deet are very good black fly repellents. Compound 21 is significantly more effective than deet at the 25% dosage providing about 10.5 hours protection. There is no significant difference between the remaining compounds and deet at the 25% dosage. Although not significantly more effective than deet, the adjusted mean for compound 20 was 0.5 and 1.5 hours greater than that of deet at the two test dosages. Compounds 7 and 35 provided about seven hours protection; compounds 20 and 47 provided over eight hours protection; compounds 6 and 33 provided about nine hours protection.

The data in Table 4 show ten compounds that exceeded deet in repellency against deer flies. Compound 20 was significantly more effective than deet with an adjusted mean protection time of 6.3 hours.

The data in Table 5 show compounds 2, 7, 20, and 35 greatly superior to deet in tests conducted in Florida against the sand fly *Culicoides mississippiensis*. Compounds 2 and 20 were also superior to deet in the Parris Island tests against *Culicoides hollensis*. Deet is considered a good repellent for sand flies (Meditsinskaya Parazitologiya i Parazitarnye Bolezni, 35 (5), 549, 1963). A biting rate of about five per hour would make the presence of sand flies tolerable to most people (Journal of Economic Entomology, 64 (1), 264, 1971). The data show certain compounds of this invention equalling or exceeding this criteria in one test and equalling or closely approaching it in the second test. The number of bites experienced by the check clearly shows very high insect pressure during these tests, emphasizing the effectiveness of the repellents.

The data in Table 6 show the relative repellency of compounds of this invention against mosquitoes when applied to skin in laboratory and field tests. Deet is an excellent mosquito repellent (The Journal of the American Medical Association, 196, 253, 1966). Repellents 33 and 34 were about equally as effective against *Aedes aegypti* as deet; repellents 19, 20, 21, and 34 were about equally as effective against *Anopheles quadrimaculatus* as deet. In field tests, repellents 2 and 20 were 1.5 and 1.4 times as effective as deet against *Aedes taeniorhynchus* and 4, 6, 7, 21, 33, and 47 were about equally as effective as deet. Because deet is such an effective mosquito repellent, chemicals having 0.5 ratios to deet are considered good mosquito repellents.

The data in Table 7 show 91 of the repellents were more effective than the standard against one species of mosquito and nine other compounds were about equally as effective as the standard. Repellents 91, 100, 101, and 115 provided outstanding protection of over 200 days and 29 other repellents provided exceptional protection of over 100 days against one species or the other. All chemicals providing 11 or more days protection are considered promising repellents.

In addition, as noted above, certain of the novel compounds of this invention are useful as cockroach repellents and certain of the amides are particularly effective against the German cockroach. The efficacy test that was used with these compounds is particularly stringent. In contrast to other test methods, where the cockroach is given an alternate choice of harborage, that is, a treated and an untreated refuge, the present method allows the insect no choice. The choice method will more frequently indicate that a material is a good repellent than does the no-choice method because the stress that is exerted on the cockroach is much reduced since the cockroach does not have to remain in the open. Under the no-choice test methods used with the compounds of this invention, if a chemical is 100% effective it means the chemical is a very strong repellent because it prevents all of the cockroaches in the test from entering a dark container that contains food and water and keeps them in an alien atmosphere. The cockroaches die rather than enter the container.

The following illustrates the unanticipated degree of effectiveness against cockroaches of certain of the repellent compounds of this invention. Bodenstein and Fales (Production Research Report No. 164, USDA, ARS, 1976) report repellency data for 872 synthetic compounds against four species of cockroach using the less stringent tests in which the roaches have a choice of harborages. Sixty of these (6.9%) provided one week of 100% protection against the German cockroach. In contrast, many of the compounds of the present invention repelled 100% of the German cockroaches and provided 100% protection for 10–17 days using the more stringent no-choice test. Hence, the extent and degree of repellency shown by many of the compounds of the present invention could not have been anticipated. Dead cockroaches are replaced at each reading period as noted later in the description of the test procedure. Overall mortality figures are included in Table 11 for repellents that lasted 17 days. These figures, when compared with the mortalities shown in Table 8 again emphasizes the effectiveness of these repellents. The cockroaches perish rather than enter the treated container. This effect becomes noticeable after about six days with an effective repellent.

Another example of the efficacy of certain of the compounds of the present invention is aptly illustrated by data in Table 8 which was obtained using a commercial cockroach repellent, MGK-874 (2-hydroxyethyl-n-octyl sulfide), and subjecting it to the same rigorous tests that were used with the compounds of this invention. Method 1 duplicates the standard test used to evaluate chemicals of the present invention. The commercial repellent does not provide one day of 100% protection. Under the most accomodating situation, Method 4, it only provides two days of 100% protection which equals the repellent protection provided by the standard repellent, fencholic acid.

Because of the stringent nature of these tests, it is anticipated that the compounds of this invention will be even more effective in a natural environmental situation where the cockroaches do have many alternate choices for harborage other than areas protected by these repellents.

The German cockroach, the test species used in obtaining the efficiency data, is considered one of the most difficult to repel or to control. Chemicals found effective against this species are generally more effective against the three other major species found in the United States, the American cockroach, *Periplaneta americana* (L.), the oriental cockroach, *Blatta orientalis* (L.), and the brownbanded cockroach, *Supella longipalpa* (F.). A test procedure that includes these four cockroach species if based on this fact, (Journal of Economic Entomology, 67, 639, 1974, Journal of Economic Entomology, 63, 429, 1970, Journal of Medical Entomology 12, 259, (1975). It is anticipated the preferred compounds of this invention will also be highly effective against other cockroach species.

The compounds of this invention are amides which gives them the advantage of possessing the chemical stability associated with this type of chemical. Another advantage it has is that the pure chemical usually possesses little odor. The ease of preparation is also a distinct advantage, usually requiring a one-step synthesis. Another advantage is that most of the acid or acid chloride and amine intermediates are available from commercial sources.

The efficacy of the amides of the present invention was demonstrated by practical tests against the German cockroach. The effectiveness of the repellents was determined by ascertaining the minimum number of days the compounds repel 100% of the test cockroaches from a treated harborage containing food and water. The amides that are highly effective as cockroach repellents are shown in Table 9, each of which provides at least one week of 100% repellency against the German cockroach. Six of the twenty-one compounds in Table 9 provided 100% repellency for a minimum of 14 days. In contrast, the 36 compounds in Table 10 provided less than seven days, usually about three days, or no repellency against the German cockroach.

For the purpose of this invention, when tested for cockroach repellency, the compounds were applied as solutes in acetone. However, other compatible liquid or solid carriers may also be used.

TEST PROCEDURE

The chemicals were evaluated for repellent activity by the method of Burden and Eastin (Pest Control 28 (6), 14, 1960) with a slight revision. The inside walls of a 237-ml (0.5-pt) cylindrical paperboard carton were coated with 0.1 g of the candidate repellent dissolved in 5 ml of acetone. Food and water were placed inside the carton after the solvent had evaporated. The cockroaches were provided access to the darkened and baited interior of the carton via a 2.0-cm-diameter hole cut in the side of the carton. The carton was set in a glass utility jar (26.5 cm high × 22.0 cm diameter) containing 25 adult male and female German cockroaches (12:13; reciprocal ratio in duplicate test). A 5-cm band of a mixture (1:1) of liquid and white petrolatum was applied along the top margin of the jar to prevent the cockroaches from escaping. Cockroaches in the treated carton were counted after 1, 2, 3, and 7 days, and every 3–4 days thereafter, until the compound became ineffective. Effectiveness was based on the length of time that 100% repellency was observed. The following classification system was used: Class 1, <100% repellency observed at intervals through seven days; Class 2, 100% repellency observed at all intervals through seven days; Class 3, 100% repellency observed at all intervals through 14 days; Class 4, 100% repellency observed at all intervals through 21 days; Class 5, 100% repellency observed at all intervals through 28 days. Dead cockroaches were replaced at three days and at each reading thereafter. All tests were duplicated and included a standard repellent, fencholic acid (3-isopropyl-1-methylcyclopentanecarboxylic acid), and an acetone check. The test environments were maintained at 27° C. and 60% RH in a daily light:dark regime of 8.5:15.5 hr, with two days of total darkness in each seven-day cycle of testing.

The foregoing examples of repellent action of these novel amides against specific insect pests is meant to be illustrative rather than limiting. For example, the compounds of the present invention can be mixed with inert ingredients or with other known insect repellents. The compounds may also be formulated or embodied into repellent compositions in the form of creams, lotions, emulsions, suspensions, solutions, dusts, and aerosol or other type of sprays.

Although insect repellents are usually applied to the skin, the compounds of this invention and formulations containing them are also useful when applied to clothing, netting, packaging, shipping containers, animals, and growing plants.

When used to repel cockroaches the compounds are usually applied in an effective cockroach repellent amount to the locus to be protected from infestation and, as noted above, can be applied in many varied forms to provide effective repellency. An effective cockroach repellent amount will vary greatly depending on the length of time that it is desired for it to be effective. The amount required in a particular situation can be readily ascertained by one skilled in the art. In a preferred method of application, the repellent compound is applied to the locus as a solution or suspension in a suitable solvent. The solutions or suspensions contain about 0.1 to 5.0 %, preferably 0.5 to 2.0 % by weight of the compound. A suitable solvent is any volatile solvent in which the compound is soluble and with which the compound will not react and which will not prevent the benefits of the invention from being realized.

TABLE 1

Physical constants of compounds synthesized in accordance with the procedures of this invention

-N(R¹)(R²)

| No. | R¹, R² | B.p. (°C./mmHg) or m.p. (°C.) | $n_D^{25}$ |
|---|---|---|---| cyclohexyl-C(=O)-N(R¹)(R²)

| No. | R¹, R² | B.p./m.p. | $n_D^{25}$ |
|---|---|---|---|
| 1 | N,N—Dimethylamino | 69–70/0.45 | 1.4794 |
| 2 | N,N—Dipropylamino | 93–5/0.45 | 1.4685 |
| 3 | N,N—Dibutylamino | 133/1.5 | 1.4675 |
| 4 | 1-Pyrrolidyl | 67–8 | |
| 5 | 1-Piperidyl | 108/0.45 | 1.5030 |
| 6 | 1-Hexahydro-1H—azepinyl | 120/0.25 | 1.5038 |
| 7 | 2-Methyl-1-piperidyl | 110–13/0.7 | 1.5001 |
| 8 | 3-Methyl-1-piperidyl | 114–16/0.45 | 1.4974 |
| 9 | 4-Methyl-1-piperidyl | 113–14/0.8 | 1.4970 |
| 10 | 2-Ethyl-1-piperidyl | 131/1.5 | 1.4970 |
| 11 | 2,6-Dimethyl-1-piperidyl | 109–11/0.5 | 1.4950 |
| 12 | 1,2,3,6-Tetrahydro-1-pyridinyl | 107–9/0.5 | 1.5175 |
| 13 | 4-Methyl-1-piperazinyl | 100–2/0.1 | 1.5041 |
| 14 | 4-Morpholinyl | 57–8 | |
| 15 | 2,6-Dimethyl-4-morpholinyl | 116–17/0.3 | 1.4919 | cyclohexenyl-C(=O)-N(R¹)(R²)

| No. | R¹, R² | B.p./m.p. | $n_D^{25}$ |
|---|---|---|---|
| 16 | N,N—Dimethylamino | 75–6/0.4 | 1.4960 |
| 17 | N,N—Dipropylamino | 88/0.15 | 1.4804 |
| 18 | N,N—Dibutylamino | 103/0.1 | 1.4775 |
| 19 | 1-Pyrrolidyl | 44–5 | |
| 20 | 1-Piperidyl | 114–15/0.2 | 1.5159 |
| 21 | 1-Hexahydro-1H—azepinyl | 105–6/0.15 | 1.5151 |
| 22 | 2-Methyl-1-piperidyl | 110–12/0.1 | 1.5106 |
| 23 | 3-Methyl-1-piperidyl | 108–10/0.1 | 1.5087 |
| 24 | 4-Methyl-1-piperidyl | 110–12/0.15 | 1.5087 |
| 25 | 2-Ethyl-1-piperidyl | 114–15/0.1 | 1.5068 |
| 26 | 2,6-Dimethyl-1-piperidyl | 112–13/0.1 | 1.5055 |
| 27 | 1,2,3,6-Tetrahydro-1-pyridinyl | 114–16/0.45 | 1.5315 |
| 28 | 4-Methyl-1-piperazinyl | 112–14/0.1 | 1.5181 |
| 29 | 4-Morpholinyl | 114–16/0.25 | 1.5194 |
| 30 | 2,6-Dimethyl-4-morpholinyl | 115–16/0.4 | 1.5043 | cyclohexyl-C(=O)-N(R¹)(R²)

| No. | R¹, R² | B.p./m.p. | $n_D^{25}$ |
|---|---|---|---|
| 31 | N,N—Dipropylamino | 100/0.7 | 1.4682 |
| 32 | N,N—Dibutylamino | 126/0.9 | 1.4669 |
| 33 | 1-Pyrrolidyl | 95/0.25 | 1.4941 |
| 34 | 1-Piperidyl | 104–6/0.5 | 1.4970 |
| 35 | 1-Hexahydro-1H—azepinyl | 115–18/0.9 | 1.5000 |
| 36 | 2-Methyl-1-piperidyl | 141–3/0.25 | 1.4930 |
| 37 | 3-Methyl-1-piperidyl | 168–70/18 | 1.4909 |
| 38 | 4-Methyl-1-piperidyl | 108/0.8 | 1.4908 |
| 39 | 2-Ethyl-1-piperidyl | 175–8/18 | 1.4930 |
| 40 | 2,6-Dimethyl-1-piperidyl | 108–10/0.5 | 1.4905 |
| 41 | 1,2,3,6-Tetrahydro-1-pyridinyl | 118–20/1.3 | 1.5100 |
| 42 | 4-Methyl-1-piperazinyl | 120–2/1.0 | 1.4990 |
| 43 | 4-Morpholinyl | 108–9/0.4 | 1.4975 |
| 44 | 2,6-Dimethyl-4-morpholinyl | 75–7 | | methylcyclohexenyl-C(=O)-N(R¹)(R²)

| No. | R¹, R² | B.p./m.p. | $n_D^{25}$ |
|---|---|---|---|
| 45 | N,N—Dipropylamino | 108/2.0 | 1.4794 |
| 46 | N,N—Dibutylamino | 120/0.45 | 1.4765 |
| 47 | 1-Pyrrolidyl | 133–6/0.2 | 1.5082 |
| 48 | 1-Piperidyl | 109/0.5 | 1.5090 |
| 49 | 1-Hexahydro-1H—azepinyl | 135/0.9 | 1.5116 |
| 50 | 2-Methyl-1-piperidyl | 120–2/1.1 | 1.5049 |
| 51 | 3-Methyl-1-piperidyl | 120–2/1.3 | 1.5035 |
| 52 | 4-Methyl-1-piperidyl | 122–4/1.0 | 1.5020 |
| 53 | 2-Ethyl-1-piperidyl | 116–18/0.5 | 1.5036 |
| 54 | 2,6-Dimethyl-1-piperidyl | 115–17/0.5 | 1.5017 |
| 55 | 1,2,3,6-Tetrahydro-1-pyridinyl | 113–15/0.7 | 1.5234 |
| 56 | 4-Methyl-1-piperazinyl | 105–7/0.3 | 1.5106 |
| 57 | 4-Morpholinyl | 104–5/0.2 | 1.5115 |
| 58 | 2,6-Dimethyl-4-morpholinyl | 122–5/0.4 | 1.4990 | bicycloheptenyl-C(=O)-N(R¹)(R²)

| No. | R¹, R² | B.p./m.p. | $n_D^{25}$ |
|---|---|---|---|
| 59 | N,N—Dipropylamino | 93–5/0.2 | 1.4900 |
| 60 | N,N—Dibutylamino | 100–2/0.1 | 1.4862 |
| 61 | 1-Pyrrolidyl | 105–8/0.15 | 1.5262 |
| 62 | 1-Piperidyl | 111–13/0.2 | 1.5244 |
| 63 | 1-Hexahydro-1H—azepinyl | 121–2/0.4 | 1.5262 |
| 64 | 2-Methyl-1-piperidyl | 108–9/0.2 | 1.5197 |
| 65 | 3-Methyl-1-piperidyl | 110–12/0.3 | 1.5169 |
| 66 | 4-Methyl-1-piperidyl | 98–100/0.1 | 1.5163 |
| 67 | 2-Ethyl-1-piperidyl | 108–9/0.15 | 1.5168 |
| 68 | 2,6-Dimethyl-1-piperidyl | 100–1/0.15 | 1.5166 |
| 69 | 1,2,3,6-Tetrahydro-1-pyridinyl | 110/0.1 | 1.5401 |
| 70 | 4-Methyl-1-piperazinyl | 103–4/0.1 | 1.5253 |
| 71 | 4-Morpholinyl | 99–100/0.1 | 1.5258 |
| 72 | 2,6-Dimethyl-4-morpholinyl | 100–2/0.1 | 1.5113 | cyclohexyl-CH₂C(=O)-N(R¹)(R²)

| No. | R¹, R² | B.p./m.p. | $n_D^{25}$ |
|---|---|---|---|
| 73 | N,N—Dimethylamino | 87–8/0.45 | 1.4780 |
| 74 | N,N—Dipropylamino | 108–9/0.45 | 1.4708 |
| 75 | N,N—Dibutylamino | 139/0.75 | 1.4698 |
| 76 | 1-Pyrrolidyl | 110–12/0.25 | 1.4977 |
| 77 | 1-Piperidyl | 109–11/0.2 | 1.5000 |
| 78 | 1-Hexahydro-1H—azepinyl | 114–16/0.2 | 1.5019 |
| 79 | 2-Methyl-1-piperidyl | 105–7/0.2 | 1.4945 |
| 80 | 3-Methyl-1-piperidyl | 118/0.4 | 1.4942 |
| 81 | 4-Methyl-1-piperidyl | 121/0.5 | 1.4935 |
| 82 | 2-Ethyl-1-piperidyl | 122–4/0.2 | 1.4943 |
| 83 | 2,6-Dimethyl-1-piperidyl | 121–3/0.3 | 1.4942 |
| 84 | 1,2,3,6-Tetrahydro-1-pyridinyl | 122–4/0.15 | 1.5114 |
| 85 | 4-Methyl-1-piperazinyl | 109/0.15 | 1.5016 |
| 86 | 4-Morpholinyl | 68–70 | |
| 87 | 2,6-Dimethyl-4-morpholinyl | 125–7/0.5 | 1.4892 | cyclohexyl-CH₂CH₂C(=O)-N(R¹)(R²)

| No. | R¹, R² | B.p./m.p. | $n_D^{25}$ |
|---|---|---|---|
| 88 | N,N—Dimethylamino | 100–2/0.4 | 1.4782 |
| 89 | N,N—Dipropylamino | 117–18/0.45 | 1.4715 |
| 90 | N,N—Dibutylamino | 133–5/0.4 | 1.4701 |
| 91 | 1-Pyrrolidyl | 126–7/0.2 | 1.4928 |
| 92 | 1-Piperidyl | 129–31/0.2 | 1.4950 |
| 93 | 1-Hexahydro-1H—azepinyl | 131–4/0.3 | 1.4985 |
| 94 | 2-Methyl-1-piperidyl | 128–30/0.35 | 1.4933 |
| 95 | 3-Methyl-1-piperidyl | 136–8/0.5 | 1.4912 |
| 96 | 4-Methyl-1-piperidyl | 136–7/0.5 | 1.4919 |
| 97 | 2-Ethyl-1-piperidyl | 126–7/0.1 | 1.4938 |
| 98 | 2,6-Dimethyl-1-piperidyl | 135/0.35 | 1.4895 |
| 99 | 1,2,3,6-Tetrahydro-1-pyridinyl | 134–5/0.5 | 1.5070 |
| 100 | 4-Methyl-1-piperazinyl | 139–40/0.1 | 1.4966 |

TABLE 1-continued
Physical constants of compounds synthesized in accordance with the procedures of this invention

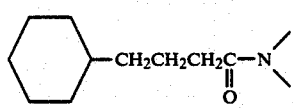

| No. | | B.p. (°C./mmHg) or m.p. (°C.) | $n_D^{25}$ |
|---|---|---|---|
| 101 | 4-Morpholinyl | 122–4/0.1 | 1.4961 |
| 102 | 2,6-Dimethyl-4-morpholinyl | 123–5/0.1 | 1.4876 |

$$\text{cyclohexyl}-CH_2CH_2CH_2\underset{\underset{O}{\|}}{C}-N\begin{subarray}{l}R^1\\R^2\end{subarray}$$

| No. | | B.p. (°C./mmHg) or m.p. (°C.) | $n_D^{25}$ |
|---|---|---|---|
| 103 | N,N—Dimethylamino | 109–10/0.4 | 1.4764 |
| 104 | N,N—Dipropylamino | 128–30/0.4 | 1.4712 |
| 105 | N,N—Dibutylamino | 148/0.4 | 1.4705 |
| 106 | 1-Pyrrolidyl | 137–9/0.4 | 1.4905 |
| 107 | 1-Piperidyl | 139–40/0.5 | 1.4920 |
| 108 | 1-Hexahydro-1H—azepinyl | 153–4/0.5 | 1.4940 |
| 109 | 2-Methyl-1-piperidyl | 142–3/0.45 | 1.4909 |
| 110 | 3-Methyl-1-piperidyl | 143–5/0.5 | 1.4882 |
| 111 | 4-Methyl-1-piperidyl | 145–7/0.45 | 1.4875 |
| 112 | 2-Ethyl-1-piperidyl | 145/0.25 | 1.4910 |
| 113 | 2,6-Dimethyl-1-piperidyl | 151–3/0.5 | 1.4874 |
| 114 | 1,2,3,6-Tetrahydro-1-pyridinyl | 145–6/0.45 | 1.5035 |
| 115 | 4-Methyl-1-piperazinyl | 134–5/0.15 | 1.4975 |
| 116 | 4-Morpholinyl | 149–51/0.45 | 1.4932 |
| 117 | 2,6-Dimethyl-4-morpholinyl | 145–7/0.45 | 1.4828 |

TABLE 2
Repellency of compounds to the stable fly *Stomoxyx calcitrans* when applied to the skin at various concentrations ethanol and compared to deet as a test standard

| No. | % Conc. | Protection time (minutes) Range | Adjusted mean | Ratio to deet[a] | No. of tests |
|---|---|---|---|---|---|
| 2 | 6.25 | 30–90 | 55 | 1.7 | 3 |
|  | 12.5 | 300–360 | 315 | 4.50[b] | 5 |
|  | 25.0 | 210–463 | 321 | 2.02[b] | 5 |
| 4 | 25.0 | 30–270 | 103 | 0.4 | 5 |
| 6 | 25.0 | 30–268 | 183 | 0.71 | 5 |
| 7 | 25.0 | 120–300 | 246 | 2.01[b] | 4 |
| 17 | 25.0 | 180–360 | 225 | 0.85 | 5 |
| 18 | 25.0 | 30–189 | 122 | 0.46 | 5 |
| 19 | 25.0 | 90–420 | 237 | 1.0 | 5 |
| 20 | 6.25 | 30–120 | 103 | 2.5[b] | 3 |
|  | 12.5 | 60–240 | 128 | 2.4[b] | 4 |
|  | 25.0 | 360–390 | 387 | 2.39[b] | 5 |
| 21 | 6.25 | 30–60 | 33 | 1.0 | 5 |
|  | 12.5 | 270–450 | 306 | 1.42 | 5 |
|  | 25.0 | 300–510 | 457 | 3.78[b] | 4 |
| 31 | 25.0 | 30–60 | 36 | 0.2 | 5 |
| 33 | 6.25 | 60–180 | 80 | 1.6 | 3 |
|  | 12.5 | 90–210 | 150 | 3.3[b] | 4 |
|  | 25.0 | 240–270 | 266 | 1.6 | 4 |
| 34 | 6.25 | 30–120 | 118 | 2.4[b] | 3 |
|  | 12.5 | 270–330 | 320 | 4.57[b] | 5 |
|  | 25.0 | 390–510 | 419 | 2.6[b] | 4 |
| 35 | 6.25 | 30–30 | 30 | 1.0 | 5 |
|  | 12.5 | 210–375 | 326 | 3.27[b] | 5 |
|  | 25.0 | 390–510 | 459 | 2.9[b] | 4 |
| 36 | 25.0 | 30–120 | 101 | 1.43 | 5 |
| 45 | 25.0 | 30–180 | 78 | 0.44 | 5 |
| 47 | 6.25 | 30–90 | 63 | 1.9 | 3 |
|  | 12.5 | 120–270 | 230 | 3.29[b] | 5 |
|  | 25.0 | 150–405 | 264 | 1.66 | 5 |
| 49 | 6.25 | 30–60 | 38 | 1.15 | 5 |
|  | 12.5 | 150–330 | 306 | 1.42 | 5 |
|  | 25.0 | 480–510 | 538 | 3.02[b] | 5 |
| 50 | 25.0 | 60–150 | 125 | 1.41 | 5 |

[a]Data compiled from a number of different tests, accounting for the fluctuation between protection time and ratio to deet among the members of the series.
[b]Significantly different from deet at the 0.05% level of confidence.

TABLE 3
Repellency of compounds applied to the skin as 12.5 and/or 25% ethanol solutions compared with deet against blackflies in two series of field tests

| No. | % Conc. | Protection time (min) Range | Adjusted mean | Ratio to deet | No. of tests |
|---|---|---|---|---|---|
| Test I (1977) ||||||
| Deet (Std) | 12.5 | 145–283 | 161 | 1.00 | 5 |
|  | 25.0 | 287–511 | 426 | 1.00 | 4 |
| 20 | 12.5 | 123–314 | 193 | 1.20[a] | 5 |
|  | 25.0 | 413–565 | 505 | 1.19[a] | 4 |
| 7 | 12.5 | 26–222 | 95 | 0.59 | 5 |
|  | 25.0 | 309–515 | 424 | 1.00[a] | 4 |
| 35 | 12.5 | 24–126 | 93 | 0.58 | 5 |
|  | 25.0 | 342–542 | 412 | 0.97[a] | 4 |
| 2 | 12.5 | 25–112 | 71 | 0.44 | 5 |
|  | 25.0 | 198–375 | 314 | 0.74[a] | 4 |
| Test II (1978) ||||||
| Deet (Std) | 25.0 | 399–623 | 520 | 1.00 | 5 |
| 6 | 25.0 | 411–628 | 537 | 1.03[a] | 5 |
| 21 | 25.0 | 524–725 | 632 | 1.21[b] | 5 |
| 33 | 25.0 | 498–603 | 554 | 1.07[a] | 5 |
| 47 | 25.0 | 425–649 | 486 | 0.94[a] | 5 |

[a]Not significantly different from deet at the 0.05% level of confidence.
[b]Significantly different from deet at the 0.05% level of confidence.

TABLE 4
Repellency of compounds applied to the skin as 25% ethanol solutions and compared with deet against deerflies in field tests (Avg. of 5 tests)

| No. | Protection time (min) Range | Adjusted mean | Ratio to deet[a] |
|---|---|---|---|
| 2 | 10–178 | 133 | 3.00 |
| 4 | 4–77 | 23 | 0.51 |
| 6 | 10–173 | 75 | 1.69 |
| 17 | 15–143 | 62 | 1.39 |
| 18 | 6–36 | 40 | 0.89 |
| 20 | 363–421 | 380 | 5.83[b] |
| 21 | 91–203 | 91 | 1.1 |
| 31 | 10–44 | 45 | 0.62 |
| 34 | 20–408 | 141 | 1.8 |
| 35 | 42–182 | 119 | 1.5 |
| 36 | 5–17 | 15 | 0.94 |
| 45 | 4–110 | 18 | 0.24 |
| 47 | 40–160 | 138 | 1.89 |
| 49 | 37–244 | 129 | 1.76 |
| 50 | 8–138 | 27 | 1.11 |

[a]Data compiled from a number of tests, accounting for the fluctuation between the protection time and ratio to deet among the members of the series.
[b]Significantly different from deet at the 0.05% level of confidence.

TABLE 5
Repellency of compounds applied to the skin as 25% ethanol solutions and compared with deet against the sandflies *Culicoides mississippiensis* and *Culicoides hollensis* in field tests

| Compounds paired | Average bites/test | Average bites/hour |
|---|---|---|
| Tests at Yankee Town, Fla. (Avg. 3 tests) |||
| Deet | 29.0 | 19.2 |
| 2 | 3.33 | 2.4 |
| Deet | 31.67 | 21.0 |
| 20 | 5.0 | 3.6 |
| Deet | 106.0 | 70.8 |
| 35 | 6.67 | 4.2 |
| Deet | 45.0 | 30.0 |
| 7 | 10.0 | 6.6 |
| Check | 1299 | 865.8 |
| Tests at Parris Island, S.C. (Avg. 3 tests) |||
| Deet | 28.7 | 18.6 |
| 20 | 9.33 | 6.0 |
| Deet | 85.0 | 54.6 |
| 2 | 16.33 | 10.8 |
| Deet | 12.0 | 7.8 |
| 7 | 16.67 | 10.8 |

TABLE 5-continued

Repellency of compounds applied to the skin as 25% ethanol solutions and compared with deet against the sandflies *Culicoides mississippiensis* and *Culicoides hollensis* in field tests

| Compounds paired | Average bites/test | Average bites/hour |
|---|---|---|
| Check | 1566 | 1277.4 |

TABLE 6

Repellency of compounds to mosquitoes when applied to the skin as 25% ethanol solutions

| | Ratio to deet | | |
|---|---|---|---|
| | Laboratory test | | Field test |
| No. | *Aedes aegypti* | *Anopheles quadrimaculatus* | *Aedes taeniorhynchus* |
| 2 | 0.22 | 0.28 | 1.5 |
| 4 | 0.22 | 0.11 | 0.77 |
| 6 | 0.14 | 0.74 | 0.82 |
| 7 | 0.70 | 0.11 | 1.15 |
| 17 | 0.24 | 0.33 | 0.52 |
| 18 | 0.13 | 0.05 | 0.07 |
| 19 | 0.20 | 0.73 | 0.44 |
| 20 | 0.68 | 1.0 | 1.4 |
| 21 | 0.64 | 0.86 | 0.7 |
| 31 | 0.24 | 0.08 | 0.45 |
| 33 | 1.12 | 0.86 | 0.69 |
| 34 | 0.89 | 1.0 | 0.34 |
| 45 | 0.23 | 0.11 | 0.12 |
| 47 | 0.28 | 0.24 | 0.99 |
| 49 | 0.55 | 0.09 | 0.65 |

TABLE 7

Repellency of compounds to mosquitoes in tests on cloth

| | *Aedes aegyptyi* Days to | | *Anopheles quadrimaculatus* Days to | |
|---|---|---|---|---|
| No. | 1st bite | 5 bites | 1st bite | 5 bites |
| 2 | 15 | 15 | 8 | 8 |
| 4 | 30 | 38 | 38 | 79 |
| 5 | 30 | 38 | 30 | 30 |
| 6 | 106 | 113 | 22 | 38 |
| 7 | 104 | 104 | 111 | 111 |
| 8 | 104 | 104 | 22 | 22 |
| 9 | 52 | 104 | 0 | 22 |
| 10 | 104 | 104 | 1 | 22 |
| 11 | 104 | 104 | 1 | 37 |
| 12 | 15 | 15 | 15 | 15 |
| 13 | 7 | 15 | 7 | 111 |
| 14 | 0 | 1 | 27 | 27 |
| 15 | 15 | 28 | 35 | 35 |
| 17 | 15 | 15 | 15 | 15 |
| 18 | 0 | 30 | 0 | 1 |
| 19 | 28 | 28 | 70 | 94 |
| 20 | 21 | 28 | 28 | 48 |
| 21 | 64 | 87 | 70 | 70 |
| 22 | 69 | 69 | 83 | 83 |
| 23 | 36 | 36 | 36 | 51 |
| 24 | 20 | 20 | 83 | 83 |
| 25 | 83 | 83 | 83 | 83 |
| 26 | 36 | 36 | 36 | 36 |
| 27 | 36 | 36 | 63 | 63 |
| 28 | 28 | 28 | 63 | 83 |
| 29 | 0 | 0 | 35 | 35 |
| 30 | 8 | 8 | 22 | 22 |
| 31 | 15 | 15 | 1 | 1 |
| 33 | 21 | 28 | 28 | 28 |
| 34 | 21 | 28 | 13 | 13 |
| 35 | 28 | 28 | 6 | 6 |
| 36 | 23 | 43 | 0 | 0 |
| 37 | 23 | 51 | 0 | 0 |
| 38 | 36 | 36 | 21 | 21 |
| 39 | 51 | 71 | 0 | 0 |
| 40 | 1 | 23 | 0 | 0 |
| 41 | 8 | 15 | 8 | 8 |
| 42 | 1 | 1 | 36 | 50 |
| 43 | 36 | 77 | 64 | 71 |

TABLE 7-continued

Repellency of compounds to mosquitoes in tests on cloth

| | *Aedes aegyptyi* Days to | | *Anopheles quadrimaculatus* Days to | |
|---|---|---|---|---|
| No. | 1st bite | 5 bites | 1st bite | 5 bites |
| 44 | 28 | 28 | 15 | 15 |
| 45 | 27 | 27 | 1 | 1 |
| 47 | 27 | 27 | 1 | 1 |
| 48 | 33 | 41 | 1 | 1 |
| 49 | 27 | 47 | 1 | 1 |
| 50 | 23 | 51 | 0 | 23 |
| 51 | 36 | 36 | 0 | 21 |
| 52 | 36 | 36 | 8 | 36 |
| 55 | 15 | 15 | 0 | 1 |
| 57 | 8 | 22 | 36 | 105 |
| 58 | 1 | 28 | 22 | 22 |
| 59 | 1 | 35 | 49 | 49 |
| 61 | 34 | 55 | 28 | 28 |
| 62 | 70 | 70 | 70 | 91 |
| 63 | 70 | 128 | 0 | 111 |
| 64 | 70 | 70 | 0 | 76 |
| 65 | 35 | 70 | 0 | 49 |
| 66 | 70 | 70 | 0 | 77 |
| 67 | 21 | 34 | 47 | 47 |
| 68 | 1 | 28 | 20 | 20 |
| 69 | 28 | 28 | 20 | 20 |
| 70 | 28 | 28 | 47 | 47 |
| 71 | 0 | 0 | 47 | 47 |
| 72 | 0 | 34 | 20 | 190 |
| 74 | 0 | 0 | 28 | 28 |
| 76 | 108 | 108 | 21 | 119 |
| 77 | 28 | 108 | 28 | 28 |
| 78 | 21 | 130 | 1 | 8 |
| 79 | 28 | 102 | 0 | 0 |
| 80 | 28 | 102 | 0 | 0 |
| 81 | 28 | 51 | 8 | 8 |
| 82 | 0 | 28 | 8 | 8 |
| 83 | 101 | 108 | 108 | 108 |
| 84 | 8 | 28 | 28 | 28 |
| 85 | 0 | 105 | 134 | 175 |
| 86 | 0 | 1 | 1 | 18 |
| 87 | 0 | 105 | 126 | 126 |
| 88 | 21 | 21 | 24 | 24 |
| 91 | 169 | 169 | 238 | 238 |
| 92 | 29 | 29 | 7 | 182 |
| 93 | 21 | 65 | 21 | 44 |
| 94 | 7 | 21 | 1 | 1 |
| 95 | 7 | 21 | 1 | 126 |
| 97 | 0 | 12 | 0 | 12 |
| 98 | 0 | 21 | 126 | 126 |
| 99 | 0 | 12 | 0 | 93 |
| 100 | 7 | 7 | 21 | 268 |
| 101 | 61 | 133 | 238 | 238 |
| 102 | 61 | 93 | 133 | 133 |
| 103 | 42 | 42 | 24 | 54 |
| 106 | 61 | 160 | 160 | 160 |
| 107 | 0 | 36 | 36 | 36 |
| 108 | 22 | 22 | 36 | 134 |
| 110 | 0 | 1 | 36 | 36 |
| 111 | 0 | 0 | 52 | 94 |
| 112 | 13 | 13 | 36 | 104 |
| 113 | 0 | 1 | 134 | 134 |
| 114 | 0 | 36 | 134 | 134 |
| 115 | 0 | 51 | 310 | 318+ |
| 116 | 77 | 134 | 134 | 134 |
| 117 | 22 | 22 | 134 | 134 |

+Compound still in test.

TABLE 8

| | % Inside Carton Day | | | | % Mortality | | | |
|---|---|---|---|---|---|---|---|---|
| Method | 1 | 2 | 3 | 7 | 1 | 2 | 3 | 7 |
| 1. Food & Water In Harborage | 1 | 8 | 10 | — | 0 | 0 | 0 | — |
| 2. Food in Harborage Water Out | 0 | 2 | .5 | 7 | 0 | 0 | 0 | 0 |
| 3. Water in Harborage Food Out | 1 | 4 | .5 | 13 | 0 | 0 | 0 | 1 |
| 4. Food & Water Out of Harborage | 0 | 0 | 2 | 6 | 0 | 0 | 0 | 0 |

TABLE 8-continued
| Method | % Inside Carton Day | | | | % Mortality | | | |
|---|---|---|---|---|---|---|---|---|
| | 1 | 2 | 3 | 7 | 1 | 2 | 3 | 7 |
| Fencholic acid Food, Water in Harborage | 0 | 0 | 10 | 80 | 0 | 0 | 0 | 0 |
| Check (Acetone) | 100 | 100 | 100 | 100 | 0 | 0 | 0 | 0 |
TABLE 9
| Compound | | Repellency Class | Min. Days 100% Effective |
|---|---|---|---|
| 1. | 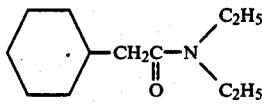 | 3 | 17 |
| 2. | 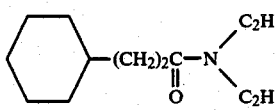 | 3 | 17 |
| 3. | 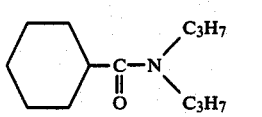 | 2 | 10 |
| 4. | 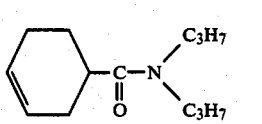 | 2 | 10 |
| 5. | 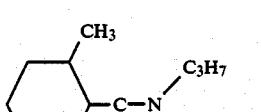 | 2 | 10 |
| 6. |  | 2 | 10 |
| 7. |  | 3 | 17 |
| 8. | 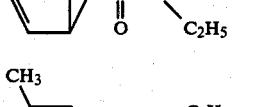 | 3 | 14 |
| 9. | 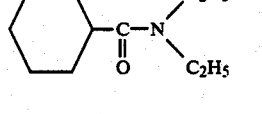 | 2 | 10 |
| 10. | 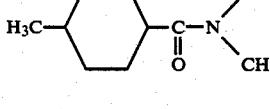 | 3 | 14 |
| 11. | 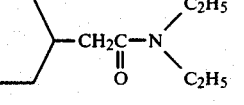 | 2 | 10 |
| 12. | 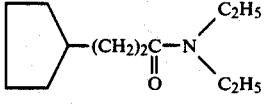 | 2 | 7 |
| 13. | 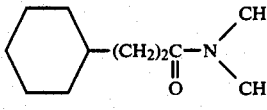 | 2 | 10 |
| 14. | 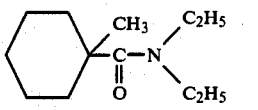 | 2 | 7 |
| 15. | 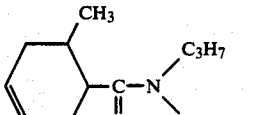 | 2 | 7 |
| 16. | 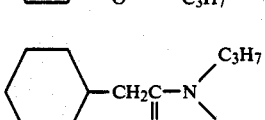 | 2 | 7 |
| 17. | 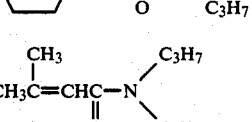 | 2 | 7 |
| 18. | 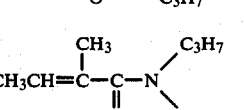 | 3 | 14 |
| 19. | 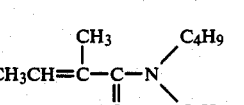 | 2 | 10 |
| 20. | 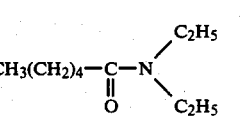 | 2 | 7 |
| 21. | 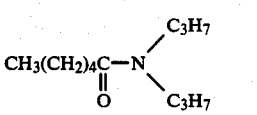 | 2 | 7 |
TABLE 10
| Compound | | Repellency Class |
|---|---|---|
| 1 | 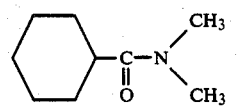 | 1 |

TABLE 10-continued
| Compound | | Repellency Class |
|---|---|---|
| 2 | 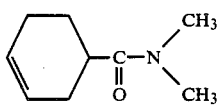 | 1 |
| 3 | 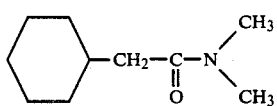 | 1 |
| 4 | 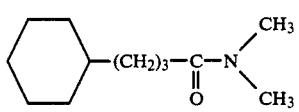 | 1 |
| 5 | 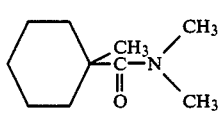 | 1 |
| 6 | 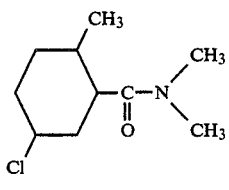 | 1 |
| 7 | 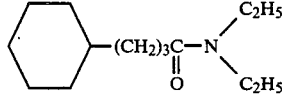 | 1 |
| 8 | 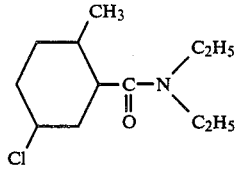 | 1 |
| 9 | 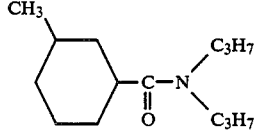 | 1 |
| 10 | 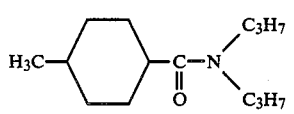 | 1 |
| 11 | 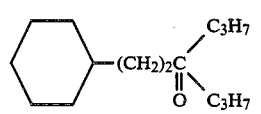 | 1 |
| 12 | 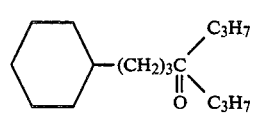 | 1 |
| 13 | 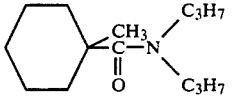 | 1 |
| 14 | 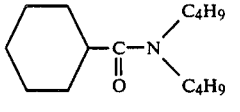 | 1 |
| 15 | 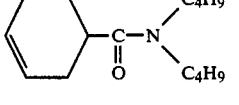 | 1 |
| 16 | 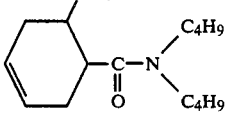 | 1 |
| 17 | 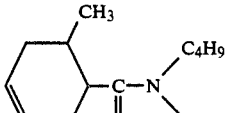 | 1 |
| 18 | 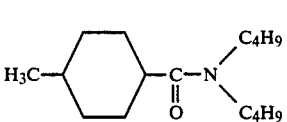 | 1 |
| 19 | 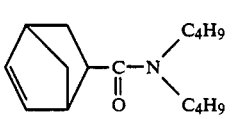 | 1 |
| 20 | 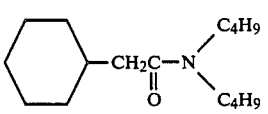 | 1 |
| 21 | 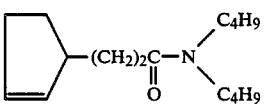 | 1 |
| 22 | 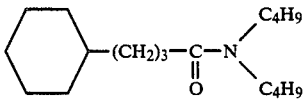 | 1 |
| 23 | 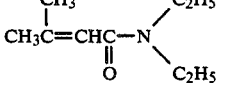 | 1 |
| 24 | 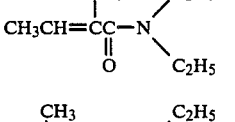 | 1 |
| 25 | 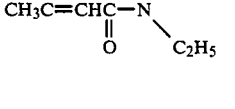 | 1 |

TABLE 10-continued

| Compound | | Repellency Class |
|---|---|---|
| 26 | CH₃C(CH₃)=CHC(O)—N(CH(CH₃)₂)(CH(CH₃)₂) | 1 |
| 27 | CH₃CH=C(CH₃)—C(O)—N(CH(CH₃)₂)(CH(CH₃)₂) | 1 |
| 28 | cyclopentyl—CH₂C(O)—N(CH₃)₂ | 1 |
| 29 | cyclopentenyl—CH₂C(O)—N(CH₃)₂ | 1 |
| 30 | cyclopentyl—(CH₂)₂C(O)—N(CH₃)₂ | 1 |
| 31 | cyclopentenyl—CH₂C(O)—N(C₂H₅)₂ | 1 |
| 32 | 3,3-dimethyl-cyclopentyl—C(CH₃)C(O)—N(C₂H₅)₂ | 1 |
| 33 | cyclopentyl—CH₂C(O)—N(C₃H₇)₂ | 1 |
| 34 | cyclopentenyl—CH₂C(O)—N(C₃H₇)₂ | 1 |
| 35 | cyclopentyl—(CH₂)₂C(O)—N(C₃H₇)₂ | 1 |

TABLE 10-continued

| Compound | | Repellency Class |
|---|---|---|
| 36 | cyclopentyl—(CH₂)₂C(O)—N(C₄H₇)(C₄H₇) | 1 |

TABLE 11

| Compound No. in Table 9 | % Morality Total % replaced through the 17–21 day period |
|---|---|
| 1 | 139 |
| 2 | 125 |
| 7 | 80 |

We claim:
1. A method of repelling cockroaches comprising applying to the cockroaches or to a locus to be protected from said cockroaches an effective cockroach repelling amount of a compound of the formula

$$R^3(O)_x(CH_2)_n-\underset{\underset{O}{\|}}{C}-N\underset{R^2}{\overset{R^1}{\diagup}}$$

wherein
$R^1$ is methyl, ethyl, propyl or butyl;
$R^2$ is methyl, ethyl, proply or butyl;
x is zero or 1;
n is zero, 1, 2 or 3;
$R^3$ is
(a) an unsubstituted saturated alicylic having 5 to 6 carbon ring members, where n is 1, 2 or 3;
(b) a substituted saturated alicyclic having 5 to 6 carbon ring members, where x is one, where the substitution is a lower alkyl in a 5 or 6 carbon ring, or the substitution is a lower alkyl at the 2 position in combination with chlorine at the 5 position in a 6 carbon ring;
(c) an unsubstituted unsaturated alicyclic having 5 or 6 carbon ring members, wherein x is one;
(d) a substituted bicyclic of the formula

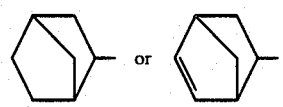

wherein the substitution is a lower alkyl at the 2 position; and
(e) an unsubstituted bicyclic of the formula

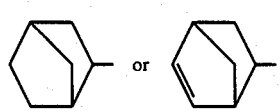

2. The method of claim 1 wherein in the compound $R^3$ is

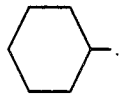
3. The method of claim 2 wherein in the compound x is zero, n is one, and each of $R^1$ and $R^2$ are ethyl.
4. The method of claim 2 wherein in the compound x is zero, n is 2, and each of $R^1$ and $R^2$ is ethyl.
5. The method of claim 1 wherein in the Compound $R^3$ is
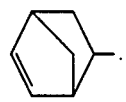
6. The method of claim 5 wherein in the compound x and n are each zero and each of $R^1$ and $R^2$ is ethyl.
* * * * *